(12) United States Patent
Muntermann

(10) Patent No.: US 7,207,987 B1
(45) Date of Patent: *Apr. 24, 2007

(54) CATHETER EXHIBITING IMPROVED ELECTRICAL PROPERTIES AS WELL AS A DEVICE AND PROCESSING METHOD FOR IMPROVING ELECTRICAL PROPERTIES OF CATHETERS

(76) Inventor: Axel Muntermann, Gotenweg 51, D-35578 Wetzlar (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/049,934

(22) PCT Filed: Aug. 16, 2000

(86) PCT No.: PCT/EP00/07942

§ 371 (c)(1),
(2), (4) Date: Aug. 7, 2002

(87) PCT Pub. No.: WO01/12091

PCT Pub. Date: Feb. 22, 2001

(30) Foreign Application Priority Data

Aug. 17, 1999 (DE) ................. 199 44 805

(51) Int. Cl.
*A61B 18/18* (2006.01)
*A61B 5/04* (2006.01)
(52) U.S. Cl. ........................ 606/41; 600/374
(58) Field of Classification Search ............ 606/41, 606/45, 46, 48–52, 1; 600/374
See application file for complete search history.

(56) References Cited

U.S. PATENT DOCUMENTS

| | | | |
|---|---|---|---|
| 4,653,500 A | | 3/1987 | Osada et al. |
| 4,896,671 A | * | 1/1990 | Cunningham et al. ...... 600/374 |
| 5,423,882 A | * | 6/1995 | Jackman et al. ............ 607/122 |
| 5,582,609 A | * | 12/1996 | Swanson et al. .............. 606/39 |
| 5,713,895 A | * | 2/1998 | Lontine et al. ................ 606/41 |
| 5,810,764 A | | 9/1998 | Eggers et al. |
| 5,991,650 A | * | 11/1999 | Swanson et al. ............ 600/374 |
| 6,047,700 A | * | 4/2000 | Eggers et al. ............... 128/898 |

FOREIGN PATENT DOCUMENTS

| | | |
|---|---|---|
| DE | 196 28 879 A1 | 7/1996 |
| DE | 197 40 976 A1 | 9/1997 |
| FR | 2 653 655 | 10/1989 |

OTHER PUBLICATIONS

International Search Report for PCT/EP00/07942.

* cited by examiner

*Primary Examiner*—Michael Peffley

(57) ABSTRACT

In order in the case of a catheter for the ablation of biological, in particular of animal or human, tissue, preferably for the ablation of human myocardial tissue, having at least one ablation or mapping electrode to permit the recording of ECG signals during catheter ablation and, in particular, to improve the quality of the recorded ECG signals to such an extent as to permit medical statements with reference to cardiac action, it is provided that the at least one ablation or mapping electrode has a reduced number of electrical interference centres. Furthermore, the invention provides methods and apparatuses with the aid of which conventional catheters can be treated in such a way that these interference centres are reduced.

24 Claims, 7 Drawing Sheets

Mapping signal before electrode treatment without applied high-frequency energy

Mapping signal after electrode treatment without applied high-frequency energy

Fig. 5

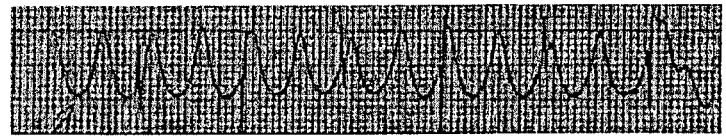

Interference in the simulated ECG signal in the case of fast, non-pulsed power regulation of the output high-frequency energy for a non-treated ablation catheter

Fig. 6

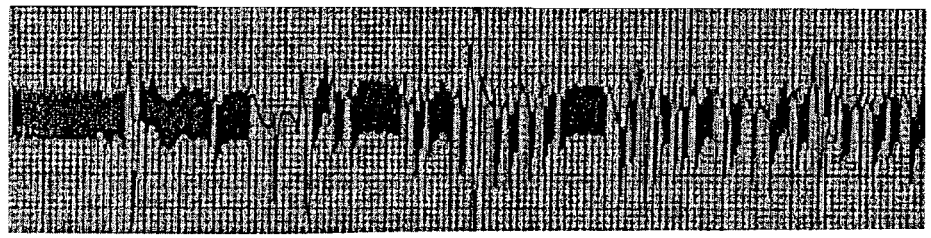

Interference in the simulated ECG signal in the case of fast, pulsed power regulation of the output high-frequency energy for a non-treated, quadrupole ablation catheter with cylindrical platinum ablation electrodes each 4 mm long

Fig. 7

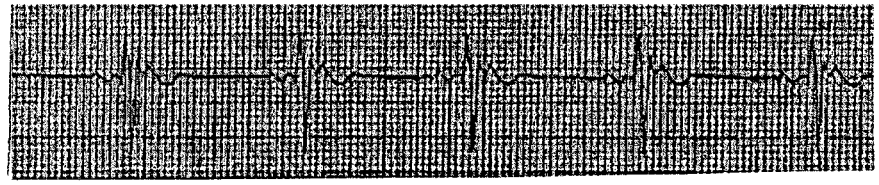

Simulated ECG signal in the case of fast, non-pulsed power regulation of the output high-frequency energy for the quadrupole ablation catheter with cylindrical platinum ablation electrodes each 4 mm long, from Fig. 6 after its treatment

Fig. 8

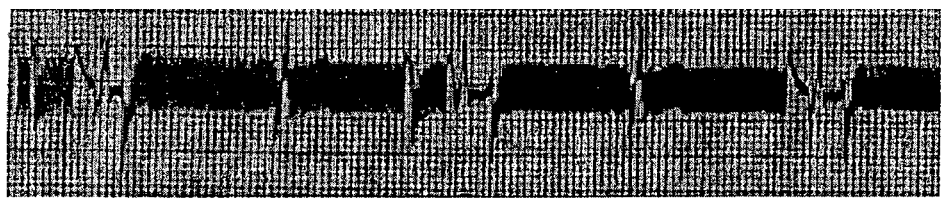

Interference in the simulated ECG signal in the case of fast, pulsed power regulation of the output high-frequency energy for a non-treated ablation catheter with a cylindrical platinum ablation electrode 4 mm long, and three further mapping electrodes

Fig. 9

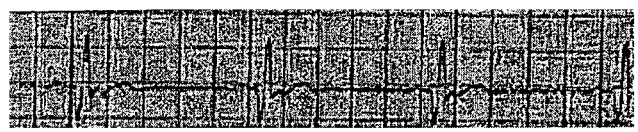

Simulated ECG signal in the case of fast, pulsed power regulation of the output high-frequency energy for the non-treated ablation catheter from Fig. 8 with a cylindrical platinum ablation electrode 4 mm long, and three further mapping electrodes after its treatment Electron microscope photograph of the platinum surface of the ablation electrode of a non-treated ablation catheter Electron microscope photograph of the platinum surface of the ablation electrode of the non-treated ablation catheter from Fig. 10

Electron microscope photograph of the platinum surface of the ablation electrode of the ablation catheter from Fig. 10

Electron microscope photograph of the platinum surface of the ablation electrode of the ablation catheter from Fig. 10

Force microscopic plot of a 10 times 10 μm surface region of an untreated platinum ablation electrode Force microscopic plot of a 10 times 10 μm surface region of a treated platinum ablation electrode

CATHETER EXHIBITING IMPROVED ELECTRICAL PROPERTIES AS WELL AS A DEVICE AND PROCESSING METHOD FOR IMPROVING ELECTRICAL PROPERTIES OF CATHETERS

CROSS-REFERENCES TO RELATED APPLICATIONS

Not applicable.

STATEMENT REGARDING FEDERALLY SPONSORED RESEARCH OR DEVELOPMENT

Not applicable.

BACKGROUND OF THE INVENTION

The invention relates to a catheter for the ablation of biological, in particular of animal or human, tissue, preferably for the ablation or mapping electrode, characterized in that the at least one ablation or mapping electrode has a reduced number of electrical interference centers that generate microscopic electric potential differences, field strength maxima or microscopically different reaction capabilities at the electrode surface, a method for treating catheters, and an apparatus for carrying out the treatment of catheters.

TECHNICAL FIELD

One of the main aims in the catheter ablation of myocardial tissue is to interrupt, by lesions of the upper layers of the heart tissue, regions of the conduction system that can have a negative effect on the cardiac action. The success of a treatment depends, however, very substantially on whether the correct depth of lesion was achieved during the ablation. In this case, correct depth of lesion means in essence that the undesired regions disrupting the conduction system are removed, but that no further-reaching injuries are introduced. It is evident that with an excessively small depth of lesion the success of treatment is endangered, whereas in some circumstances an excessively large depth produces very many relatively severe side effects. Since there are vessel walls running in the heart which may not be unnecessarily damaged, and also the tissue to be ablated is frequently only of a limited thickness, in the event of excessively large depths of the lesions it is even possible for lethal accidents to occur because of severed heart walls or heart vessels. An attempt has therefore been made in the case of conventional ablation methods to estimate the optimum depth of lesion by the synchronous recording of ECG signals on the occurrence of success in treatment. However, in this case the irradiated high-frequency energy was exceptionally detrimental to the recording of these signals, and an attempt was undertaken to mitigate such influences by means of appropriate electrical or electronic filters in the downstream equipment. However these attempts had only limited success, or none. Producing the irradiated power led to extremely long treatment times which are in the range of several hours and in this case both subject the patient to substantial stress and are unable to reliably prevent slippage of the ablation catheter. Furthermore, lesion is no longer possible starting from a specific power, since the temperature generated no longer suffices for tissue coagulation.

SUMMARY OF THE INVENTION

It is therefore the object of the invention to permit the recording of ECG signals during catheter ablation and, in particular, to improve the quality of the recorded ECG signals to such an extent as to permit medical statements with reference to cardiac action.

This object is achieved by the invention in an exceptionally surprising way with the aid of a catheter for the ablation of biological, in particular of animal or human, tissue, including ablation of human myocardial tissue, said catheter comprising: at least one ablation or mapping electrode, wherein the at least one ablation or mapping electrode has a reduced number of electrical interference centres which generate microscopic electric potential differences, field strength maxima or microscopically different reaction capabilities at the electrode surface and wherein the at least one ablation or mapping electrode has an electrolytically treated surface. This object is also achieved by a method for producing a catheter with improved electrical properties, the method comprising the following steps:

providing a catheter which comprises at least one ablation or mapping electrode, providing a vessel with a solution which contains ions whose motion can be influenced by an electrical field, immersing the at least one ablation or mapping electrode in the solution, providing a further electrode in contact with the solution, treating the at least one ablation or mapping electrode, by applying an electric voltage between the ablation or mapping electrode.

This object is also achieved by Apparatus for catheter treatment, comprising:

a vessel for holding an electrolytic solution and regions of the catheter, an electrolytic solution in the vessel, wherein the ablation or mapping electrode and the further electrode can be wetted by the electrolyte during conducting of the catheter treatment, a voltage-generating or current-generating unit, and connection device for connecting at least one ablation or mapping electrode of the catheter and a further electrode to the voltage-generating or current-generating unit.

The inventor surprisingly followed a completely different path than has previously been the case in the known prior art.

Instead of subjecting the recording equipment to change or an attempt at improvement, the cause of interference in the recording of the ECG signals were reduced or even completely eliminated.

The inventor was the first to find out that the cause of the electrical interference in the ECG recording during simultaneous irradiation of high-frequency energy essentially resides not in the leads to and from the catheter electrodes, not in the electronic recording devices and, in particular, not in their input filters, but in electrical interference centres in the region of the surface of the ablation or mapping electrodes.

This finding was all the more surprising since every investigated ablation catheter with platinum electrodes exhibited such electrical interference centres, and after their reduction or removal, essentially after their removal from the electrode surface, was virtually or completely free from the undesired interference previously described.

In accordance with the invention, in the case of a catheter for the ablation of biological, in particular animal or human, tissue, preferably for the ablation of human myocardial tissue, having at least one ablation or mapping electrode, this at least one ablation or mapping electrode has a reduced number of electrical interference centres. For example, this improves the disturbed ECG recordings illustrated in FIGS. 5 and 6 in such a way that the signals illustrated in FIG. 7 or 9 can be obtained. It was also established, surprisingly, that the ECG signals were substantially improved even without an applied high frequency, that is to say exhibited distinctly fewer interference signals.

In a particularly advantageous way, the electrical interference centres which generate electric signals during the output of high-frequency energy to the at least one ablation or mapping electrode and which are essentially arranged on surface regions of the at least one ablation or mapping electrode are reduced in their number, areal extent and/or electrical effect. This results in a removal or electrical deactivation of the influence of these interference centres.

A particularly effective method for achieving the above successes consists in that the at least one ablation or mapping electrode has an electrolytically treated surface. An electrolytic method for rounding small tubular medical articles is known from DE 196 28 879 A1. In this method, a cathodal pin of defined diameter is inserted into the cavity, and an electrical potential is generated by applying an electric current between the internal pin and one that is connected to the anode, electrolytic internal deburring at corners and edges being achieved by adding an electrically conducting electrolyte.

In the electrolytic treatment, that is to say a treatment with the aid of an electrolyte and an applied voltage or impressed current, it is particularly advantageous when the treatment is carried out with a solution containing halogen ions, in particular chlorine ions, because then it is possible to observe atomic rearrangement processes on the metal surface, in particular on the platinum surface, which lead to an altered surface structure which has the desired positive properties.

It was frequently to be observed after this treatment that structures of the surface of the at least one ablation or mapping electrode have a rounded surface structure whose edges have a radius of more than approximately 500 nm, preferably of more than 100 nm, but at least more than 10 nm, and it is suspected that these surface changes already cause at least a portion of the reduction in the electrical interference centres or their effects.

It could be established after the treatment, with the aid of optical investigations of the discolorations of a platinum ablation electrode surface, for example, that the at least one ablation or mapping electrode comprises a metal whose atoms are present at the surface in a fashion bound at least partially atomically or in an amorphous and essentially non-crystalline manner. It is assumed by virtue of this rearrangement or electrolytic deposition by galvanic deposition processes that electric potentials present at the surface are compensated, for example, by grain boundaries in the metal, which is present in crystalline form, and that after the treatment according to the invention it is possible to balance out even microscopic electric crystalline potential differences, regions with field strength maxima or microscopically different reactive capabilities at the electrode surface. This mitigates the phenomena occurring, for example, during the output of HF energy, which are ascribed without limitation of the generality or the scope of the invention to locally differing ionic mobility, the point being that there is no longer any "turning on" by more strongly bound or less mobile polar ions which would cause the formation of electric potentials that are superimposed on the ECG signal. The ions which now move virtually identically at all locations on the surface of the ablation or mapping electrode no longer generate local field strength differences and also no longer disturb the ECG recording.

It is therefore assumed that, when the catheter advantageously comprises a platinum ablation or mapping electrode, the surface of an ablation or mapping electrode is coated at least partially with elementary platinum. It is, however, also within the scope of the invention for such an atomic, essentially non-crystalline or amorphous coating also to be produced, for example, using electroplating deposition techniques or generally known techniques for coating or plating.

It then results in an advantageous way that the surface of the at least one ablation or mapping electrode comprises regions with deposited metal present essentially in an amorphous manner or atomically.

In the case of the method for producing a catheter with improved electrical properties, in the case of which method the catheter comprises at least one ablation or mapping electrode, the ablation or mapping electrode, of the catheter, that is to be treated is immersed in a solution which contains ions whose motion can be influenced by an electric field; this is advantageously achieved by virtue of the fact that an electric voltage which generates the motion of the ions is applied between the ablation or mapping electrode, of the catheter, that is to be treated and a further electrode in contact with the solution. The ions to be moved onto the catheter electrode surface strike there and, both with the aid of their electric fields and, for example, their dipole moment or energy potentials of the atomic or molecular electron cloud and their kinetic energy, create interactions at the metal surface which measurably give rise to the desired electrical consequences of the atomic rearrangement or deposition.

The method can be carried out with particular advantage when the solution contains NaCl in a range from 0.1 to 100 g/l. Furthermore, there is a particularly preferred range when the solution contains NaCl in an amount of approximately 7 g/l.

Depositions at the ablation or mapping electrode surface are achieved, for example, whenever the solution contains ions of a metal salt. Prior surface treatments, for example in the case of platinum-iridium catheters, have aimed at enlarging the surface, that is to say precisely to create structures that are not too smooth but rough, having a surface that is larger approximately by the factor 1000; however, the invention proceeds, with surprising success, precisely along the opposite path.

Good results are achieved with the aid of an applied AC voltage containing components which have a frequency of more than 0.01 Hz and less than 10 kHz. The particularly preferred frequency range extends from 1 to 100 Hz and is most strongly preferred to be at about 10 Hz.

Good results are achieved when the applied AC voltage is in a range from 0.1 to 100 $V_{eff}$. The range most strongly preferred results when the applied AC voltage is at 3 to 7 $V_{eff}$.

Instead of an applied voltage, it is also possible to impress an AC current which generates a voltage having the properties set forth above on the ablation or mapping electrode and the further electrode. The best results follow in this case when the AC voltage has, per ablation or mapping electrode, a current intensity of from about 1 $mA_{eff}$ to 1 $A_{eff}$, preferably from 30 to 100 $mA_{eff}$.

An advantageous apparatus for catheter treatment comprises a vessel for holding electrolytic solution and regions of the catheter as well as, during the conduct of the catheter treatment, an electrolytic solution, and a connection device for connecting at least one ablation or mapping electrode of the catheter and a further electrode to a voltage-generating or current-generating unit, in the case of which apparatus the ablation or mapping electrode and the further electrode can be wetted by the electrolyte during the conduct of the treatment.

In the case of a compact, transportable embodiment that can be used on site directly before treatment, the voltage-generating or current-generating unit is an internal unit mechanically connected to the vessel.

In the case of a cost-effective stationary apparatus, the voltage-generating or current-generating unit is an external unit not mechanically connected to the vessel, for example an external laboratory voltage generator.

BRIEF DESCRIPTION OF THE DRAWINGS

The invention is explained in more detail below with the aid of preferred embodiments and with reference to the attached drawings, in which:

FIG. 5 shows interference in the simulated ECG signal in the case of fast, non-pulsed power regulation of the output high-frequency energy for a non-treated ablation catheter, FIG. 6 shows interference in the simulated ECG signal in the case of fast, pulsed power regulation of the output high-frequency energy for a non-treated, quadrupole ablation catheter with cylindrical platinum ablation electrodes each 4 mm long, FIG. 7 shows a simulated ECG signal in the case of fast, non-pulsed power regulation of the output high-frequency energy for the quadrupole ablation catheter with cylindrical platinum ablation electrodes, each 4 mm long, from FIG. 6 after its treatment, FIG. 8 shows interference in the simulated ECG signal in the case of fast, pulsed power regulation of the output high-frequency energy for a non-treated ablation catheter with a cylindrical platinum ablation electrode 4 mm long, and three further mapping electrodes, FIG. 9 shows a simulated ECG signal in the case of fast, pulsed power regulation of the output high-frequency energy for the non-treated ablation catheter from FIG. 8 with a cylindrical platinum ablation electrode 4 mm long, and three further mapping electrodes after its treatment.

DETAILED DESCRIPTION OF THE INVENTION

The invention is described below in more detail and with reference to the attached drawings.

Figure 1:
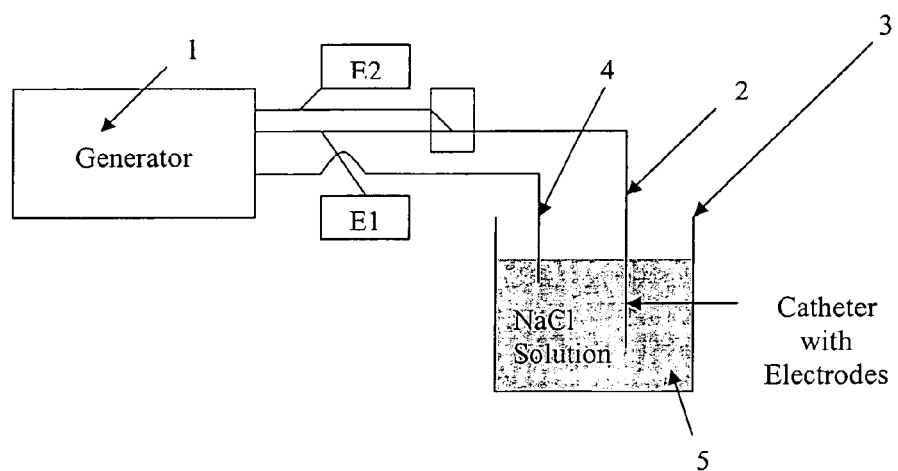
FIG. 1 shows a schematic illustration of an apparatus for treating ablation catheters.

Reference is firstly made to FIG. 1 from there may be gathered a generator 1, which is connected to a catheter 2, and a vessel 3 filled with electrolyte.

In the example from FIG. 1, the catheter is provided with at least one ablation or mapping electrode, which is connected to the generator 1 via a supply lead E1, and with a. further electrode, which is connected to the generator 1 via a supply lead E2. The further electrode can be a mapping or an ablation electrode.

Suitable as catheters for carrying out the invention are essentially all known ablation catheters, in particular catheters with platinum electrodes, and the following specified catheters, for example, were used successfully in the investigations of the inventor:

1. BARD SideWinder Catheter S/N: 17009000
2. BARD SideWinder Catheter S/N: 1300013000
3. Cordis Webster Catheter Internal S/N: CW1
4. Cardiac Pathways Catheter S/N: G709313
5. Biotronic Catheter: AlCath Twin (non-ablation catheter, fractal Pt/Ir surface)
6. BARD Stinger Distal Tip ablation catheter 4 mm Tip
8. BARD Stinger Distal Tip ablation catheter 8 mm Tip
9. Biotronic Catheter AlFractal, Distal Tip
10. Ablation catheter (fractal Pt/Ir surface)

Use was made as generator 1 of a conventional laboratory alternating current generator which could generate frequencies in the range from 0.01 Hz to 10 kHz. During the treatment of the catheter 1, which had platinum electrodes in the present embodiment, voltages were applied in a frequency range from 1 to 100 Hz, preferably at 10 Hz, whose root-mean-square voltages were in a range from 0.1 to 100 $V_{eff}$.

A particularly preferred range was from 1 to 10 $V_{eff}$, and the most preferred AC voltage range was from 3 to 7 $V_{eff}$. As alternative to the voltage generator, it was possible to use a current generator which was regulated in the range from 1 $mA_{eff}$ to 1 $A_{eff}$, preferably in a range from 30 to 100 $mA_{eff}$, this current intensity being applied per ablation or mapping electrode.

This voltage or this current was generated between the at least one ablation or mapping electrode of the catheter 2 and the further electrode, connected via the supply lead E2, or was generated between the electrode connected via the supply lead E1 and a further electrode 4 in contact with the electrolytic solution 5, the catheter 2 having been immersed with the electrodes to be treated in the electrolytic solution 5.

Figure 2:
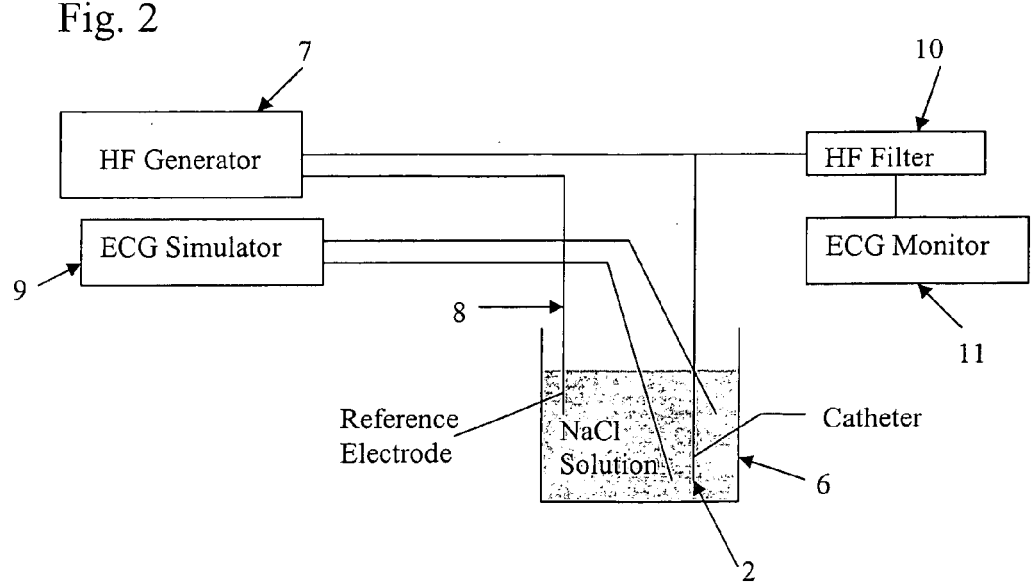
FIG. 2 shows a schematic illustration of an apparatus for measuring simulated ECG signals with and without irradiated high-frequency energy.

These voltages or current intensities were applied over a current period of from approximately 1 second to several minutes, it being possible for measurements in the set-up illustrated in FIG. 2 to show that a saturation could be achieved in each case which was accompanied by the virtually complete disappearance of interference signals. Thereafter, further treatment no longer yielded noticeable advantages.

Furthermore, it was also possible to treat more than one ablation or mapping electrode at the same time, for example in the case of a catheter comprising four ablation electrodes in the case of which only the required current intensity rose, in order to produce the same positive effect in the same time period for a plurality of electrodes. It was possible in this case to apply voltages, or to impress currents, both to neighbouring catheter electrodes and to the further electrode 4.

Use was made as electrolytic solution of a halogen-ion-containing solution which preferably contained chlorine ions and, in a way most preferred, an NaCl solution.

The concentration of an NaCl solution was in a range from 0.1 to 100 grams per liter and was preferably approximately 7 grams per liter, which corresponds approximately to a physiological sodium chloride solution. For lower concentrations, only longer treatment times resulted in conjunction with approximately equally good results.

The catheters were essentially left in the electrolytic solution 5 until the desired current-reducing value of the signal transmission quality referred to the ECG signal was yielded upon application of AC voltage at high frequency.

In order to check the result, use was made of the set-up illustrated in FIG. 2, which included a vessel 6 which had a physiological NaCl solution and in which the catheter 2 was arranged in such a way that its ablation or mapping electrode was completely wetted by the NaCl solution, while the catheter 2 was also connected to a conventional high-frequency generator 7 which was used to feed the ablation electrode of the catheter 2 with the high-frequency energy values typical of ablation.

The HF field was generated by the HF generator 7 between the ablation electrode of the catheter 2 and a reference electrode 8, and in this way represented to a very good approximation a situation such as also obtains in the human heart, for example.

An ECG simulator 9 was used to generate voltage signals which corresponded to a very good approximation to the electric voltages output by the human heart, both in terms of level and of their time profile.

The catheter 2 was also connected to a high-frequency filter 10 which filtered out the high-frequency signal components fed in by the HF generator 7. Such filter arrangements are well known to the person skilled in the art and can correspond, for example, to the input filters used in the Quadra Pulse unit from AD Electronic.

The ECG signal obtained, as tapped from the catheter, in particular from its mapping electrode, or even its ablation electrode, was then fed to an ECG monitor 11 such as is marketed, for example, by Physiocontrol under the designation of LIFEPAK 10 or by Bard as EP-Laborsystem.

The results obtained are explained in more detail below with reference to FIGS. 3 to 9.

Figure 3:
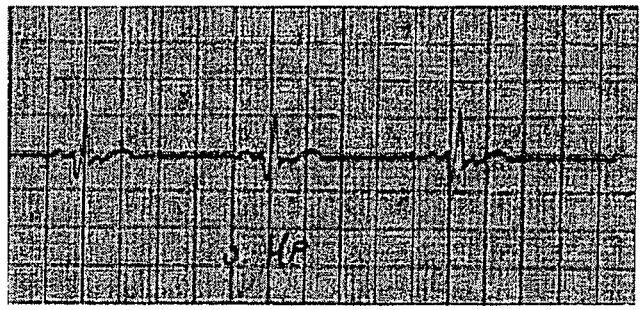
FIG. 3 shows a simulated ECG signal, as mapping signal, before electrode treatment without applied high-frequency energy.
Figure 4:
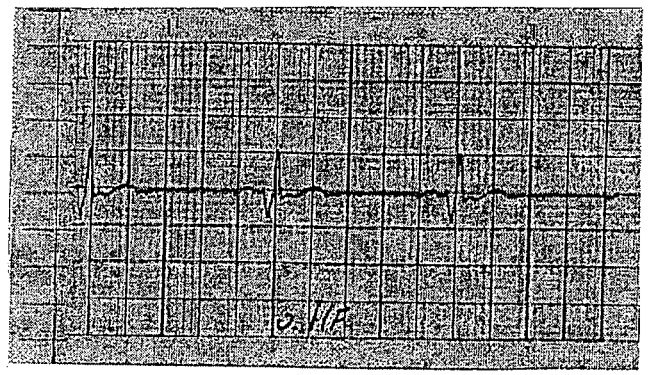
FIG. 4 shows a simulated ECG signal, as mapping signal, after electrode treatment without applied high-frequency energy.

As long as no high-frequency energy or high-frequency voltage was fed to the catheter electrodes, FIGS. 3 and 4 prove that the recording of the ECG signals could be undertaken virtually without interference.

However, if the level of the high-frequency voltage or the amount of irradiated high-frequency energy is regulated during the ECG recording, as is the case during a real ablation procedure on the patient, voltages arise which vary virtually linearly in proportion to the irradiated energy and are illustrated, for example, in FIG. 5.

Regulation of the output energy in the course of a power regulation of the irradiated high-frequency energy therefore always leads to superimposition of interference signals on the ECG signals, which renders it impossible, as a rule, for the physician to make a statement on the success of treatment or the current condition of the heart.

Even more difficult is the situation in the case of pulsed power regulation, as illustrated in FIGS. 6 and 8, in which figures it is virtually no longer possible to detect any components of the ECG signal at all.

The high-frequency power irradiated in the case of these experiments was from approximately 1 to 50 W, as is entirely normal for high-frequency catheter ablation in human hearts.

However, if an ablation catheter was treated in the way described above, it was possible in conjunction with the same experimental set-up to reduce the superimposed interference down to a value virtually no longer measurable, in any case by a factor of more than ten, as is illustrated, for example, in FIGS. 7 and 9.

The ECG result illustrated in FIG. 7 corresponds essentially to the set-up and the respective values which lead in the case of an untreated catheter to the results shown in FIG. 5, while the results illustrated in FIG. 9, which were obtained with a catheter treated according to the invention, corresponded to those which were shown in FIGS. 6 and 8 for the untreated catheter.

The experimental set-up, identical per se in each case, which differed only in whether the catheter was used directly as marketed by the respective manufacturer or whether it was treated in the way according to the invention, proves the great success of the present invention unambiguously.

The catheters according to the invention therefore have on their electrode surfaces fewer electric or electronic interference centres which can generate the superimposed signals. The measure of the reduction in interference is therefore a measure of the presence or the reduced or diminished presence of such interference centres.

It is assumed without limitation of generality and without limiting the invention that the generation of such signals superimposed on the ECG signal is due to local adhesion sites or local extremes in the electric field strength on the surface of the catheter, at which ions or molecules of dipole moment can be bound with differing strength or accelerated, and can then, upon application of the HF voltage or HF energy, generate, because of the different mobility, a voltage signal which is superimposed on the ECG signal.

Figure 10:
FIG. 10 shows an electron microscope photograph of the platinum surface of the ablation electrode of a non-treated ablation catheter with 1 960-fold magnification.
Figure 11:
FIG. 11 shows an electron microscope photograph of the platinum surface of the ablation electrode of the non-treated ablation catheter from FIG. 10 with 6 160-fold magnification.
Figure 12:
FIG. 12 shows an electron microscope photograph of the platinum surface of the ablation electrode of the ablation catheter from FIG. 10 with 2 040-fold magnification after its treatment.
Figure 13:
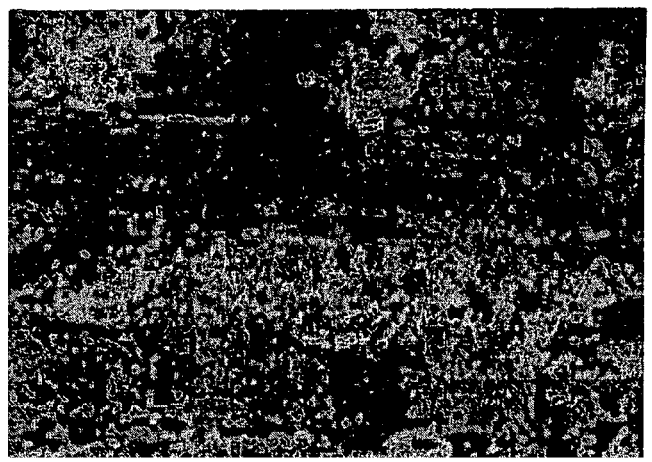
FIG. 13 shows an electron microscope photograph of the platinum surface of the ablation electrode of the ablation catheter from FIG. 10 with 6 080-fold amplification after its treatment.

The electron microscope photographs illustrated in FIGS. 10 to 13 were obtained in order to provide proof of such behaviour: as in the case of FIGS. 10 and 11, for example, they show that the catheter surface, initially sharp edged in the microstructure region, has soft roundings and fewer sharp ridges or furrows after the electrolytic treatment.

The mechanical smoothing alone can reduce the mechanical friction of the ions on the surface, thus diminishing interference centres brought about thereby which are mechanically caused but electrically active.

Furthermore, it was possible by optical investigations to prove the deposition or the presence of elementary platinum on the treated surface of the ablation or mapping electrode. This led to the assumption that crystalline grain boundaries or other suitable surface regions of the platinum, for example regions with sharp edges and high electric field strengths, are affected by the attack of the chlorine ions and platinum or metal atoms can be dissolved out. Platinum atoms can become detached from the metallic crystalline compound and be rearranged in an amorphous manner by the kinetic energy and/or the potentials of the electron cloud of the chlorine ions.

A virtual detachment, that is to say a migration in the bound state of the platinum atom, also results in release of the atom from the crystal compound, and its rearrangement.

The rounded tips of the treated surface, which are exposed to increased attack, can also be explained thereby, the point being that attack from several sides can take place precisely in these regions.

A further alternative explanation consists in that the halogen ions cause the ion milling known from the vacuum processing of semiconductors, in the case of which mechanical removal takes place at the surface.

Figure 14:
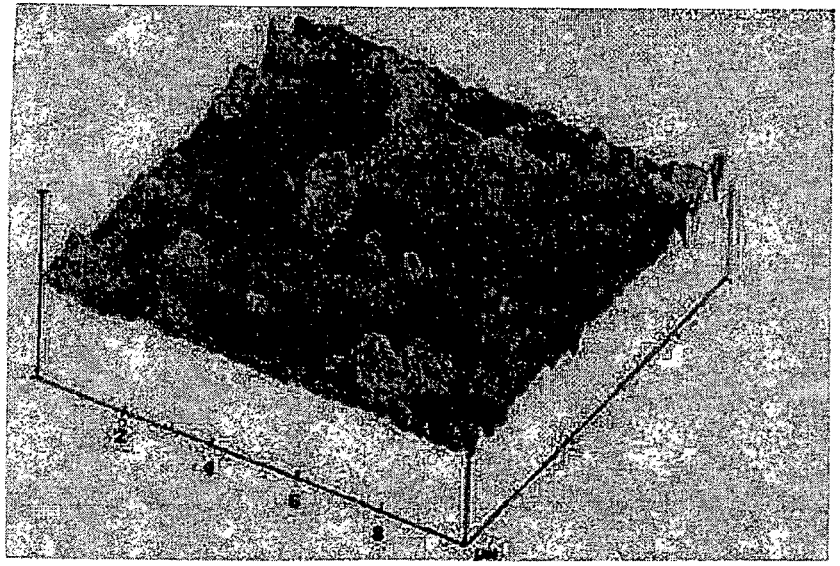
FIG. 14 shows an AFM (atomic force microscopic) or force microscopic plot of a surface region of size 10 times 10 μm of an untreated platinum ablation electrode.
Figure 15:
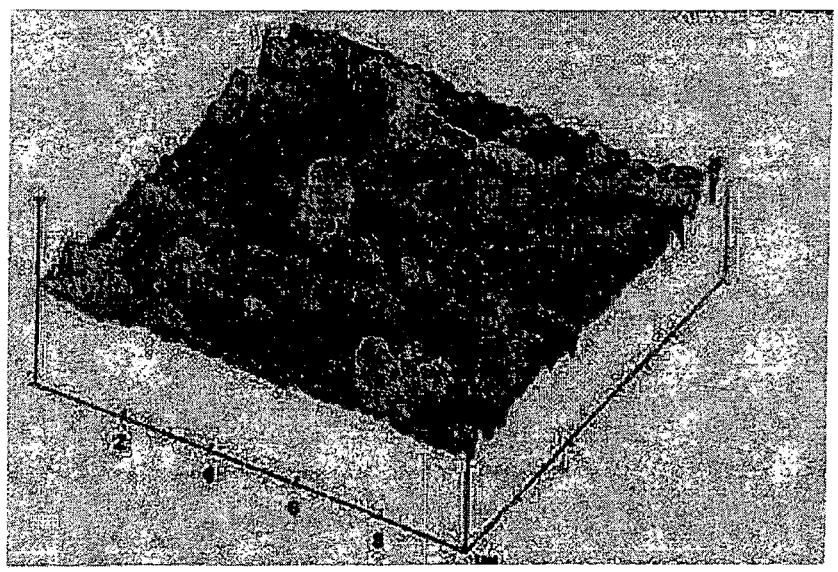
FIG. 15 shows an AFM or force microscopic plot of a surface region of size 10 times 10 μm of a treated platinum ablation electrode.

The difference caused by the treatment also become very particularly clear on the force microscopic plots which show, for example in FIG. 14, the untreated surface with pin-like extensions and sharp ridges and, in the case of the treated surface which is illustrated in FIG. 15, a entirely smooth surface without pin-like extensions.

This migration of platinum atoms can also compensate potentials present at the surface, for example at grain boundaries, or field strength maxima in such a way that even the effective electrical influence of such solid-state potentials or field strength maxima can be drastically reduced.

It is therefore possible to reduce not only the areal extent of the electrical interference centres present before the treatment, but also their electrical effect.

The inventors also found out that in many cases associated with a treated catheter structures of the surface of the ablation or mapping electrode no longer have sharp edges, that is to say very small radii of curvature. In a surface section with a length, width or height of less than 10 µm, the edges present had a radius of more than approximately 10 to 50 µm.

Sharper edges or smaller radii are either regularly reduced in number or no longer occur at all. In accordance with the invention, most radii of curvature of the edges were more than approximately 500 nm, preferably more than 100 nm, but at least more than 10 nm.

It is also within the scope of the invention for metal salts to be dissolved instead of the halogen ions or in addition to the halogen-ion-containing electrolytic solution, in order in this way to achieve an electroplating amorphous deposition of metal atoms on the metallic ablation or mapping electrode.

It may be pointed out that catheters treated according to the invention exhibit a clearly improved signal quality, that is to say substantially smaller interference signals, even without applied high-frequency energy. This improvement is not limited to ablation electrodes, but can also be used successfully in the case of mapping electrodes or mapping catheters.

The invention claimed is:

1. Method for producing a catheter with improved electrical properties, the method comprising the following steps:
   providing a catheter which comprises at least one ablation or mapping electrode,
   providing a vessel with a solution which contains ions whose motion can be influenced by an electrical field,
   immersing the at least one ablation or mapping electrode in the solution,
   providing a further electrode in contact with the solution,
   treating the at least one ablation or mapping electrode, by applying an electric voltage between the ablation or mapping electrode.

2. Method according to claim 1, characterized in that the further electrode is an electrode of the catheter.

3. Method according to claim 1, characterized in that the further electrode is an external electrode.

4. Method according to claim 1, characterized in that the solution contains halogen ions.

5. Method according to claim 4, characterized in that the solution contains chlorine ions.

6. Method according to claim 1, characterized in that the solution contains NaCl in a range from 0.1 to 100 g/l.

7. Method according to claim 6, characterized in that the solution contains NaCl in an amount of approximately 7 g/l.

8. Method according to claim 1, wherein the solution contains ions of a metal salt.

9. Method according to claim 1, characterized in that the applied voltage is an AC voltage.

10. Method according to claim 9, characterized in that the applied AC voltage contains components which have a frequency of more than 0.01 Hz and less than 10 kHz.

11. Method according to claim 9, characterized in that the applied AC voltage contains components which are in a frequency range from 1 to 100 Hz.

12. Method according to claim 1, characterized in that the applied AC voltage is in a range from 0.1 to 100 $V_{eff}$.

13. Method according to claim 11, characterized in that the applied AC voltage is in a range from 1 to 10 $V_{eff}$.

14. Method according to claim 11, characterized in that the applied AC voltage is at 3 to 7 $V_{eff}$.

15. Method according to claim 1, characterized in that an AC current which generates an AC voltage is impressed on the ablation or mapping electrode and the further electrode.

16. Method according to claim 15, characterized in that the AC voltage has, per ablation or mapping electrode, a current intensity of from 1 $mA_{eff}$ to 1 $A_{eff}$.

17. Apparatus for catheter treatment comprising:
   a vessel for holding an electrolytic solution and regions of the catheter,
   an electrolytic solution in the vessel,
   an ablation or mapping electrode,
   wherein the ablation or mapping electrode can be wetted by the electrolyte during conducting of the catheter treatment,
   a voltage-generating or current-generating unit, and
   a connection device for connecting at least one ablation or mapping electrode of the catheter and a further electrode to the voltage-generating or current-generating unit, wherein
   the voltage-generating or current-generating unit comprises an internal unit mechanically connected to the vessel.

18. Catheter for the ablation of biological, in particular of animal or human tissue, including ablation of human myocardial tissue, said catheter comprising at least one ablation or mapping electrode, produced with a method comprising the following steps:
   providing a catheter which comprises at least one ablation or mapping electrode,
   providing a vessel with a solution which contains ions whose motion can be influenced by an electrical field,
   immersing the at least one ablation or mapping electrode in the solution,
   providing a further electrode in contact with the solution,
   treating the at least one ablation or mapping electrode, by applying an electric voltage between the ablation or mapping electrode.

19. Catheter according to claim 18, characterized in that said ablation or mapping electrode has a reduced number of electrical interference centres which generate microscopic electric potential differences, field strength maxima or microscopically different reaction capabilities at the electrode surface.

20. Catheter according to claim 18, characterized in that the surface of the at least one ablation or mapping electrode has a rounded surface structure whose edges or tips have a radius of curvature of more than 10 nm.

21. Catheter according to claim 18, characterized in that the surface of the at least one ablation or mapping electrode is coated at least partially with elementary platinum.

22. Catheter according to claim 18, characterized in that the at least one ablation or mapping electrode comprises a metal whose atoms are present at the surface in a fashion bound at least partially atomically or in an amorphous manner and in an essentially non-crystalline manner.

23. Catheter according to claim 18, characterized in that at least one ablation or mapping electrode comprises platinum.

24. Catheter according to claim 18, characterized in that the surface of the at least one ablation or mapping electrode comprises regions with deposited metal present essentially in an amorphous manner or atomically.

* * * * *